US00PP08628P

United States Patent [19]

Zary

[11] Patent Number: Plant 8,628

[45] Date of Patent: Mar. 8, 1994

[54] HYBRID TEA ROSE PLANT NAMED 'JACABLE'

[75] Inventor: Keith W. Zary, Thousand Oaks, Calif.

[73] Assignee: Bear Creek Gardens, Inc., Medford, Oreg.

[21] Appl. No.: 991,630

[22] Filed: Dec. 15, 1992

[51] Int. Cl.[5] ..... A01H 5/00

[52] U.S. Cl. ..... Plt./12

[58] Field of Search ..... Plt. 11, 12, 16, 20

*Primary Examiner*—Howard J. Locker

*Attorney, Agent, or Firm*—Klarquist, Sparkman, Campbell, Leigh and Whinston

[57] ABSTRACT

Hybrid tea rose plant having distinctive bicolored flowers on stems of consistent length, thick petals, long vase life, vigorous upright growth habit and pleasing fragrance.

1 Drawing Sheet

1

The present invention relates to a new and distinct variety of rose plant of the hybrid tea class which was originated by me by crossing the variety Jacara, U.S. Plant Pat. No. 6,316, with the variety Korlingo, U.S. Plant Pat. No. 5,846.

The primary objective of this breeding was to produce a new rose variety having the flower production and bicolor effect of the female parent combined with the excellent petal substance and flower form of the male parent. The objective was substantially achieved along with other desirable improvements as evidenced by the following unique combination of characteristics which are outstanding in the new variety and which distinguish it from its parents, as well as from all other varieties of which I am aware:

1. Vigorous, upright growth habit;
2. Long vase life;
3. Pleasant, moderately strong fragrance;
4. Bicolored flowers;
5. Thick petal substance;
6. Stems of consistent length.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color description using terminology in accordance with The Royal Horticultural Society (London) Colour Chart, except where ordinary dictionary significance of color is indicated.

Parentage:

*Seed parent.*—Jacara, U.S. Plant Pat. No. 6,316.

*Pollen parent.*—Korlingo, U.S. Plant Pat. No. 5,846.

Classification:

*Botanical.*—Rosa hybrida.

*Commercial.*—Hybrid tea.

2

FLOWER

Observations made from specimens grown in a garden in Somis, Calif., from March through August, 1992.

Blooming habit: Recurrent.

Bud:

*Size.*—1½ inches when the petals start to unfurl.

*Form.*—Long, pointed ovoid.

*Color.*—When sepals first devide, bud color is Red Group 43B. When half blown, the upper sides of the petals are Red Group 43B; and the lower sides of the petals are Red Group 43D on the outer (guard) petals changing to White Group 155D on the lower half of the inner petals.

*Sepals.*—Color: Green Group 138B with a reddish overlay. Surface texture: Covered in fine hairs. There are three normally appendaged sepals. There are two unappendaged sepals with hairy edges.

*Receptacle.*—Color: Green Group 139C. Shape: Funnel. Size: Medium (⅜×5/16 inch). Surface: Covered in very fine hairs.

*Peduncle.*—Length: Medium (3½ to 4 inches). Surface: Prickly and glandular. Color: Medium green and bronzy. Strength: Stiff, erect.

Bloom:

*Size.*—Large. Average open size is 5 to 5½ inches.

*Borne.*—Singly.

*Stems.*—Medium, strong (14 to 18 inches).

*Form.*—When first open: High centered. Permanence: Retains its form to the end.

*Petalage.*—Number of petals under normal conditions: 30 to 35.

*Color.*—The upper side of petals is Red Group 43B. The reverse side of the petals is Red Group 43D to White Group 155D. The base of the petals have a small, greenish-white half moon (¼×¼ inches) at the point of attachment. The major color on the upper side is Red Group 43B.

*Variegations.*—None.

*Discoloration.*—The general tonality at the end of the first day: No change. At the end of the third day: No change.

*Fragrance.*—Moderate.

Petals:

*Texture.*—Thick.

*Shape.*—Round.

*Form.*—Tips slightly recurved

*Arrangement.*—Imbricated, with few petaloids in the center.

*Persistence.*—Hang on and dry.

*Lastingness.*—On the plant: Long (6 days). As a cut flower: Long (7 to 8 days).

Reproductive Parts:

*Anthers.*—Size: Medium. Quantity: Many. Color: Yellow. Arrangement: Regular around styles.

*Filaments.*—Color: Reddish.

*Pollen.*—Color: Lemon yellow.

*Styles.*—Color: Reddish.

*Stigmas.*—Color Greenish white.

Form: Bush.

Growth: Vigorous, upright, branching.

Foliage: Number of leaflets on normal mid-stem leaves: 5.

*Size.*—Small for a hybrid tea (4 to 4½×3 to 3½ inches).

*Quantity.*—Sparse.

*Color.*—New foliage: Dark green with reddish underside. Old foliage: Dark green; semi-glossy.

Leaflets:

*Shape.*—Pointed oval.

*Texture.*—Upper side: Leathery, semi-glossy.

*Edge.*—Serrated.

*Serration.*—Single, small.

*Petiole rachis.*—Color: Green with a reddish blush.

*Petiole underside.*—Smooth with occasional prickles.

*Stipules.*—Short, serrated.

*Disease resistance.*—Susceptible to mildew, but resistant to rust under normal growing conditions at Somis, Calif.

Wood:

*New wood.*—Color: Reddish. Bark: Smooth.

Old wood.—Color: Green. Bark: Smooth.

Prickles:

*Quantity.*—On main canes from base: Ordinary. On laterals from main canes: Ordinary.

*Form.*—Medium, hooked downward.

*Color when young.*—Red.

Small prickles:

*Quantity.*—On main stalks: Few. On laterals: Few.

*Color.*—Brown.

I claim:

1. A new and distinct variety of rose plant of the hybrid tea class, substantially as herein shown and described, characterized particularly as to novelty by the unique combination of its bicolored flowers on stems of consistent length, thick petals, long vase life, vigorous upright growth habit and pleasing fragrance.

* * * * *

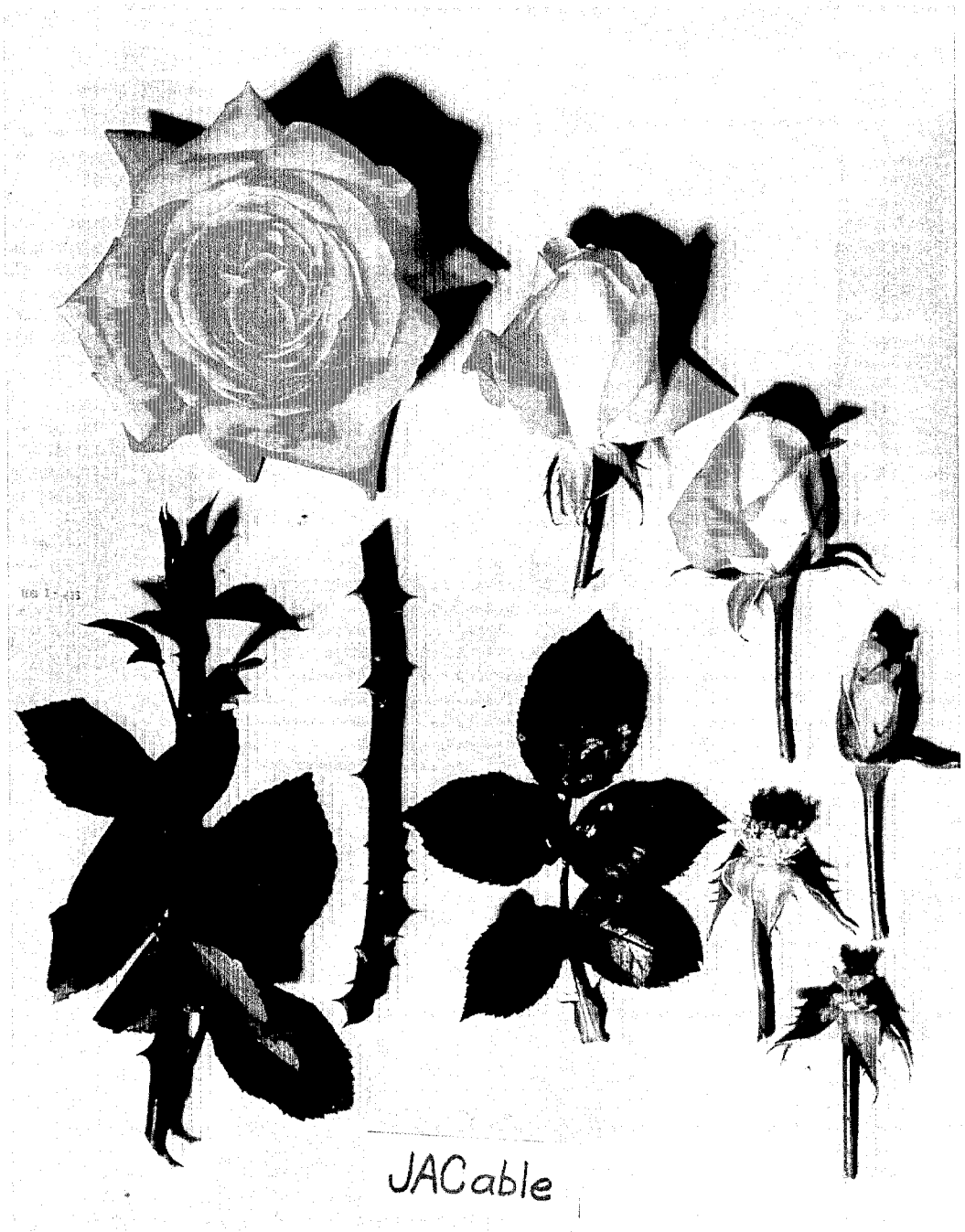
JACable